(12) United States Patent
Zimmermann et al.

(10) Patent No.: US 8,925,334 B2
(45) Date of Patent: Jan. 6, 2015

(54) CRYOGENIC STORAGE DEVICE

(75) Inventors: Heiko Zimmermann, St. Ingbert (DE);
Uwe Schoen, Neunkirchen (DE);
Guenter R. Fuhr, Berlin (DE); Dirk Leuthold, Brahmenau (DE); Marianne Belke, Jena (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 362 days.

(21) Appl. No.: 13/129,870

(22) PCT Filed: Nov. 9, 2009

(86) PCT No.: PCT/EP2009/008000
§ 371 (c)(1),
(2), (4) Date: May 18, 2011

(87) PCT Pub. No.: WO2010/057589
PCT Pub. Date: May 27, 2010

(65) Prior Publication Data
US 2011/0219788 A1    Sep. 15, 2011

(30) Foreign Application Priority Data
Nov. 19, 2008  (DE) .......................... 10 2008 057 981

(51) Int. Cl.
*F25D 13/06* (2006.01)
*F17C 3/10* (2006.01)
(Continued)

(52) U.S. Cl.
CPC ................ *A01N 1/0252* (2013.01); *G01N 1/42* (2013.01); *G01N 2035/00435* (2013.01)
USPC ..................... 62/63; 62/440; 62/48.3; 62/378

(58) Field of Classification Search
USPC ................................ 62/48.1, 48.3, 49.2, 52.1
See application file for complete search history.

(56) References Cited

U.S. PATENT DOCUMENTS

| 4,969,336 A | 11/1990 | Knippscheer et al. |
| 5,029,447 A | 7/1991 | Richard |

(Continued)

FOREIGN PATENT DOCUMENTS

| DE | 10202304 A1 | 7/2003 |
| DE | 10332799 A1 | 2/2005 |

(Continued)

OTHER PUBLICATIONS

International Search Report for PCT/EP2009/008000.

*Primary Examiner* — Judy Swann
*Assistant Examiner* — Zachary R Anderegg
(74) *Attorney, Agent, or Firm* — Caesar, Rivise, Bernstein, Cohen & Pokotilow, Ltd.

(57) ABSTRACT

The invention relates to a cryogenic storage device and to a method for operating a cryogenic storage device, particularly for cryogenic storage of biological samples, comprising a sample carrying device that is set up to accommodate samples, a cryogenic container that is set up to accommodate the sample carrying device, a container cooling device with which the cryogenic container can be cooled, an intermediate storage container that is set up for intermediate storage of the sample carrying device, a transport device with which the sample carrying device can be moved between the cryogenic container and the intermediate storage container and a sensor device with which at least one operating parameter of the cryogenic storage device can be registered. The transport device is set up to be activated in dependence on an output signal from the sensor device upon registering a predetermined operating condition of the cryogenic storage device, so that the sample carrying device is moved from the cryogenic container to the intermediate storage container. Additionally or alternatively, an intermediate storage cooling device that is set up for cooling the intermediate storage container can be activated in dependence on an output signal of the sensor device.

5 Claims, 7 Drawing Sheets

(51) Int. Cl.
   *F25D 25/00*   (2006.01)
   *F25D 11/00*   (2006.01)
   *A01N 1/02*   (2006.01)
   *G01N 1/42*   (2006.01)
   *G01N 35/00*   (2006.01)

(56) References Cited

U.S. PATENT DOCUMENTS

| | | | |
|---|---|---|---|
| 5,125,240 A * | 6/1992 | Knippscheer et al. | 62/266 |
| 5,233,844 A * | 8/1993 | Knippscheer et al. | 62/440 |
| 2004/0187515 A1* | 9/2004 | Shu et al. | 62/378 |
| 2005/0069861 A1 | 3/2005 | Zimmermann et al. | |
| 2005/0260102 A1* | 11/2005 | Angelantoni et al. | 422/102 |
| 2006/0156753 A1* | 7/2006 | Fuhr et al. | 62/378 |
| 2007/0199596 A1* | 8/2007 | Fernandez | 137/228 |
| 2007/0267419 A1 | 11/2007 | Fuhr et al. | |
| 2008/0092581 A1* | 4/2008 | Schumann et al. | 62/378 |
| 2008/0213080 A1 | 9/2008 | Cachelin et al. | |

FOREIGN PATENT DOCUMENTS

| | | |
|---|---|---|
| DE | 102004047965 A1 | 4/2006 |
| EP | 1939561 A2 | 11/2007 |
| WO | 2005010499 A2 | 2/2005 |
| WO | 2007024540 A1 | 3/2007 |

\* cited by examiner

CRYOGENIC STORAGE DEVICE

BACKGROUND OF THE INVENTION

The invention relates to a cryogenic storage device, in particular for the cryogenic storage of biological samples, and to a method for operating a cryogenic storage device.

It is known in biology, biotechnology, pharmacology and medicine to store samples of biological material in a frozen state. In order to maintain the vitality of the samples over a relatively long period of time, very low temperatures are required for this, for example, the temperature of liquid nitrogen or of liquid nitrogen vapor. A recrystallization in the samples, which could result in the sample material being destroyed, can be avoided for months and years at such low temperatures. Such cryogenic samples are usually stored in cryogenic containers which are usually vacuum-insulated, known as cryogenic tanks. Such cryogenic tanks can be cooled for example by liquid nitrogen which is located in a liquid bath at the bottom of the cryogenic tank. The samples are often stored on shelves, known as racks, which in the gas phase are arranged above the liquid nitrogen. Such a cryogenic tank is disclosed for example in DE 103 32 799 A1. In order to maintain the cooling for a long period of time, usually a refilling with liquid nitrogen is necessary.

During storage of the biological samples, it is important that the samples on the one hand do not come into contact with the cooling fluid and on the other hand are also not unduly heated. Such mistakes can lead to an irretrievable loss of the sample material. In particular, the maintaining of sufficient cooling is very important for the quality of the cryogenic storage. When refilling the cryogenic container with liquid nitrogen, however, an overfilling with liquid nitrogen may occur under some circumstances. In this case, the samples in the racks arranged above the liquid reservoir may come into contact with the liquid nitrogen and may thus be destroyed. In order to avoid any overfilling of the nitrogen reservoir at the bottom of the cryogenic container, therefore, filling level sensors and automatic valve control mechanisms are used. Particularly at the aforementioned low temperatures, however, failure of a filling level sensor or of the fluid valves regulating the supply of nitrogen may occur, which may lead to overfilling.

Another risk to the samples lies in a heating of the samples, which can lead to a recrystallization or in the worst case to a melting of the samples. This may be caused for example as a result of defective insulation of the cryogenic container. Since a loss of samples may occur in the event of such malfunctions, there is a need to protect the samples stored in the cryogenic tank in the event of a malfunction.

It is therefore an objective of the invention to provide an improved cryogenic storage device and an improved method for operating a cryogenic storage device, by means of which the abovementioned problems can be avoided. In particular, it is an objective of the invention to provide a device and a method by means of which it is possible to prevent the samples stored therein or stored in this way from being destroyed or damaged as a result of one of the malfunctions mentioned above.

The object is achieved by a device and a method according to the invention.

SUMMARY OF THE INVENTION

The invention comprises the general technical teaching to transfer samples which are stored in a cryogenic tank, and which are at risk due to an occurring malfunction, into an intermediate storage container while maintaining the cooling chain. In particular, according to the teaching of the invention, a certain operating state of a cryogenic storage device can be detected and the samples can be transferred accordingly.

A cryogenic storage device according to the invention, which is suitable for the cryogenic storage of biological samples, comprises a sample carrier device which is adapted to accommodate the biological samples. The sample carrier device may be configured for example in the form of shelves, known as racks. It may be made in one piece or may consist of a plurality of carrier parts. The cryogenic storage device furthermore comprises a cryogenic container which is adapted to accommodate the sample carrier device, and a container cooling device by means of which the cryogenic container can be cooled. Such a cryogenic container is established for example by a vacuum-insulated cryogenic tank, at the bottom of which there is located a reservoir of liquid coolant, e.g. nitrogen, which forms the container cooling device. Liquid nitrogen can be refilled via an optionally provided external supply device for liquid coolant. The liquid nitrogen may be supplied for example periodically or on a demand-controlled basis or by a user. In order to detect a demand, a filling level sensor or a temperature sensor may be provided in the cryogenic container. The cryogenic tank is for example cylindrical with a round base area and an opening on its round upper side for loading and unloading the sample carriers. Advantageously, the cryogenic container has a thermally insulated closure device, by means of which the opening in the cryogenic container is releasably closed in the stored state. The sample carrier device is preferably adapted to the shape of the cryogenic tank. By way of example, it consists of a plurality of carrier parts in the form of racks shaped as sectors of a cylinder. In the normal operating state, i.e. for example during storage of the samples, the sample carrier parts are preferably located in an interior of the cryogenic container. The sample carrier device is then preferably formed by the entirety of all the carrier parts that can be accommodated in the interior of the cryogenic container.

A cryogenic storage device according to the invention comprises an intermediate storage container which is adapted for the intermediate storage of the sample carrier device, and a transport device by means of which the sample carrier device can be moved between the cryogenic container and the intermediate storage container. The intermediate storage container is preferably suitable for accommodating for intermediate storage purposes the entire sample carrier device consisting of all the carrier parts that can be accommodated in the interior of the cryogenic container. To this end, the interior of the intermediate storage container preferably has a volume that is greater than or equal to the volume of the interior of the cryogenic container. The intermediate storage container is advantageously thermally insulated and has an interior in which the sample carrier device can be accommodated for intermediate storage purposes. So that it is possible to see into the interior, the intermediate storage container may have an at least partially transparent container wall. The intermediate storage container may be adapted to the shape of the cryogenic container and may have e.g. a cylindrical shape. The intermediate storage container is preferably adapted to accommodate either a portion of the sample carrier device stored in the cryogenic container or the entire sample carrier device, i.e. all the sample carrier parts stored in the cryogenic container. In the event of a defective sample carrier part, it is then sufficient for example if only the defective sample carrier part is moved into the intermediate storage container for replacement purposes. On the other hand, it is then possible, for example when there is a risk of overfilling with nitrogen in the cryogenic container, to transfer all the sample carrier parts into the intermediate storage container and thus to protect said parts.

By way of example, the intermediate storage container forms a storage tower with a closable opening on its underside, which is positioned over the opening on the upper side of the cryogenic container. The intermediate storage container and the cryogenic container are preferably arranged in such a way that the interiors thereof are linked to one another when the closure devices are open. Direct transport of the sample carrier device can thus take place from the interior of the cryogenic container into the interior of the intermediate storage container and vice versa. Since the sample carrier device may in general consist of a plurality of carrier parts that can be moved separately from one another, individual carrier parts can also be moved between the intermediate storage container and the cryogenic container by the transport device.

According to the invention, the cryogenic storage device additionally has a sensor device by means of which at least one operating parameter of the cryogenic storage device can be detected. Upon detection of a predetermined operating state of the cryogenic storage device, the transport device can be activated as a function of an output signal from the sensor device so that the sample carrier device is moved from the cryogenic container into the intermediate storage container. A predetermined operating state of the cryogenic storage device is for example a malfunction state of the cryogenic storage device or simply a refilling state during a refilling with liquid nitrogen. In this application, a malfunction state or malfunction is deemed to be an undesirable operating state of the cryogenic storage device, through which the samples could be placed at risk. This may also concern an operating state which is brought about by a malfunction independent of the cryogenic storage device, for example a fire.

According to a preferred variant embodiment of the cryogenic storage device according to the invention, the latter comprises in addition to the container cooling device also an intermediate storage cooling device, by means of which the intermediate storage container can be cooled. Like the transport device, this intermediate storage cooling device can also be activated as a function of an output signal from the sensor device upon detection of a predetermined operating state of the cryogenic storage device, in order to cool the intermediate storage container. The intermediate storage cooling device can preferably be activated independently of the container cooling device for the cryogenic container. The intermediate storage cooling device is preferably also actuated during a regular removal or introduction of samples into or from the cryogenic storage device.

The method according to the invention for operating a cryogenic storage device comprising a cryogenic container which is cooled by a container cooling device, an intermediate storage container which is adapted for the intermediate storage of a sample carrier device, and a transport device by means of which the sample carrier device can be moved between the cryogenic container and the intermediate storage container, comprises the steps: cryogenically storing biological samples, which are arranged in a sample carrier device, in a cryogenic container, and detecting at least one operating parameter of the cryogenic storage device by means of a sensor device. According to the invention, upon detection of a predetermined operating state of the cryogenic storage device, the transport device is activated as a function of an output signal from the sensor device and the sample carrier device is moved from the cryogenic container into the intermediate storage container. In addition or as an alternative, an intermediate storage cooling device for cooling the intermediate storage container is activated as a function of an output signal from the sensor device and the intermediate storage container is cooled. Preferably, an alarm indicator is additionally activated to output an acoustic or optical alarm signal.

Advantageously, upon detection of a malfunction state, firstly the intermediate storage cooling device is activated and then the transport device is activated in order to transport the sample carrier device into the intermediate storage container which has already been cooled. It is thus possible to ensure that the cooling chain is maintained during sample storage.

The intermediate cooling device is advantageously suitable for cooling the intermediate storage container to different temperatures. Preferably, the cooling can also be controlled at different rates and with a different coolant demand. For example, in the event of a malfunction, it may be necessary to transport the samples very quickly from the cryogenic container into the intermediate storage container. It is then necessary under some circumstances to cool the intermediate storage container very quickly to a certain temperature, which may then also take place with a relatively high coolant demand. On the other hand, for economic reasons, it is not always desirable to cool the intermediate storage container particularly quickly or to a very low temperature with maximum coolant consumption. When cooling the intermediate storage container, substantially cold nitrogen gas is made to flow into the intermediate storage container while moist air or another gas mixture is forced out of the intermediate storage container and blown out through an outlet valve. Besides the cooling, this has the effect that moisture is removed from the intermediate storage container, as a result of which it is possible to prevent any ice formation on the samples.

In the method according to the invention, a cooling of the intermediate storage container is generally provided before transporting a sample carrier device from the cryogenic container into the intermediate storage container, in order to prevent any thawing of the samples in the intermediate storage container. To this end, cooling to different temperatures is required depending on the length of time for which the samples are being transferred into the intermediate storage container. By way of example, for a short residence of the samples in the intermediate storage container for a duration of less than 5 minutes, it is sufficient if the intermediate storage container is cooled to a temperature between $-10°$ C. and $0°$ C. For a longer residence of the samples in the intermediate storage container of up to 15 minutes, a cooling to $-30°$ C. is advantageous. For a residence of the samples in the intermediate storage container of up to 90 minutes, a storage temperature of $-80°$ C. in the intermediate storage container is advantageous. At this temperature, recrystallizations in the samples can be reliably avoided for a relatively long period of time. For even longer storage of the samples in the intermediate storage container of up to 12 hours, the temperature of the intermediate storage container is lowered to a temperature between $-80°$ C. and $-140°$ C.

In order to detect the at least one operating parameter of the cryogenic storage device, the sensor device preferably comprises at least one sensor. Examples of possible types of sensor which may be used in the sensor device of the cryogenic storage device according to the invention and in the method according to the invention are mentioned below.

In order to detect the temperature on the sample carrier device, in the cryogenic container and/or in the intermediate storage container, a sample carrier temperature sensor, a container temperature sensor and/or an intermediate storage temperature sensor may be provided.

In order to detect a coolant consumption of the cooling device, a coolant sensor may be provided. In this case, separate coolant sensors may be provided for the container cooling device and the intermediate storage cooling device, or else one common sensor for a common coolant supply source. The same applies to detecting an operating state of a coolant valve of the container cooling device and/or of the intermediate storage cooling device, for which one or more throughflow sensors may be provided. In order to measure the filling level of the coolant in the cryogenic container, a filling level sensor may be provided.

In order to visually monitor the samples, preferably at least one camera device is provided which is adapted to record images in the intermediate storage container or in the cryogenic container. The detection of the at least one operating parameter may accordingly also comprise a recording of images in the intermediate storage container and/or in the cryogenic container by means of a camera device.

Furthermore, the sensor device may also comprise a pressure sensor which is adapted to detect a negative pressure in an evacuated wall of the cryogenic container. The state of the vacuum insulation of the cryogenic container can thus be monitored.

The detection of the at least one operating parameter of the cryogenic storage device may also comprise the detection of an operating state of the sample carrier device. To this end, a sample carrier test sensor may be provided. Furthermore, the sensor device may comprise at least one gas sensor for detecting a gas composition in the cryogenic container and/or in the intermediate storage container. Finally, a time measuring unit may also be provided which is adapted to detect a duration of time, for example a duration for which the sample carrier device is located in the intermediate storage container.

Preferably, a plurality of operating parameters of the cryogenic storage device are detected in order to recognize a predetermined operating state. The sensor device therefore preferably comprises a plurality of the aforementioned types of sensor for determining the operating parameters.

In order to avoid a relatively long opening of the cryogenic storage device and an associated heating of the interior during the loading of the cryogenic storage device and during the removal of samples therefrom, the cryogenic storage device according to the invention preferably comprises a lock device. This is adapted for introducing and removing samples into and from an interior of the intermediate storage container. Cryogenic samples can thus be introduced through the lock device into the intermediate storage container, where they can be introduced into a rack. As soon as the samples are located in the rack, said samples can be inserted into the actual cryogenic container by means of the transport device. For the handling of the samples in the lock device, the lock device preferably has at least one hand access and one viewing window.

In a preferred embodiment of the invention, the intermediate storage container comprises a storage tower which is arranged on the upper side of the cryogenic container, and an intermediate storage closure device by means of which the interior of the storage tower can be releasably closed. A storage tower is a bell-like or hood-like container with a bottom opening facing toward the cryogenic container.

The storage tower can sit with its opening over the opening of the cryogenic tank and can close off the latter, so that the two interiors are linked to one another. By means of the intermediate storage closure device, the interior of the storage tower can in this case be cut off from the interior of the cryogenic tank. The intermediate storage closure device and the closure device for the cryogenic tank can also be closed simultaneously. The storage tower can also be spatially separated from the cryogenic tank, for example by lifting it off the latter. As an alternative, the cryogenic tank may be lowered relative to the storage tower. The intermediate storage closure device may be thermally insulated, so that the contents of the intermediate storage container are protected when the cryogenic container and the intermediate storage container are spatially separated from one another. The intermediate storage closure device and the closure device for the cryogenic container may consist for example of one or more closure caps or doors. Closure devices composed of multiple parts are also possible, which allow different-sized openings of the cryogenic container and intermediate storage container. Preferably, the intermediate storage closure device comprises a removable base plate which inter alia can prevent cold nitrogen gas from falling downward out of the intermediate storage container.

According to a preferred variant of the method according to the invention, it is advantageous if the interior of the intermediate storage container is closed by the intermediate storage closure device once a sample carrier device has been moved from the cryogenic container into the intermediate storage container.

In a storage tower, a winch is fitted for example at an upper end of the storage tower. A movement of the sample carrier device then takes place by means of the winch in the upward or downward direction between the cryogenic container and the intermediate storage container. As an alternative or in addition, the transport device may comprise a robot arm, an extendable rod or a rail. In addition to a winch, a translation mechanism is also useful, by means of which the sample carrier device can be moved horizontally. The transport device may also be used for the regular removal or introduction of samples into and from the cryogenic storage device.

Preferably, the cryogenic storage device comprises a control device which, together with the sensor device and the transport device, forms a control loop. The control device is preferably adapted to detect a malfunction state of the cryogenic storage device. Operating parameters of the cryogenic storage device that are detected by the sensor device are output to the control device. The latter determines an operating state on the basis of the sensor signals and operating parameters. An operating state may be a malfunction state, for example an overfilling with liquid nitrogen, an undue heating of the samples, diminishing insulation of the cryogenic tank, or else a defective rack, a defective cryogenic container, or the like. However, the operating states must not be malfunction states. It may also be a refilling state during the regular refilling of nitrogen, or the ascertainment of a certain duration of time for which the sample carrier device has been located in the intermediate storage container. Depending on the detected operating state, control signals for activation purposes are then sent by the control device to the transport device and/or the intermediate storage cooling device.

For operation of the cryogenic storage device, it is advantageous if certain operating modes are provided for different predetermined operating states. By way of example, the risk of overfilling with liquid coolant exists mainly while coolant is being supplied to the cryogenic container. It is therefore provided according to a preferred variant of the method according to the invention to transport the sample carrier device by way of precaution into the intermediate storage container and to leave it there while coolant is being supplied to the cryogenic container.

If the sample carrier device comprises a plurality of carrier parts, it may be useful for example upon detection of an overfill or upon detection of another predetermined operating state to move all the carrier parts simultaneously into the intermediate storage container. This has the advantage that all the sample carrier parts can be simultaneously and rapidly protected.

In the event of a defective cryogenic container or a defective sample carrier device, the defective part must generally be replaced. In this case, a further operating mode is advantageous. This comprises transporting the sample carrier device or a carrier part thereof into the intermediate storage container and then spatially separating the intermediate storage container and the cryogenic container, for example by lowering or raising one part. In addition, a horizontal displacement of the cryogenic container and intermediate storage container relative to one another may be useful. A defective sample carrier device can then be pulled downward out of the intermediate storage container and replaced. A defective cryogenic container can be replaced before the two parts are brought back together. Advantageously, the intermediate storage container and the cryogenic container are brought together only once the replaced components have been cooled back to their operating temperature.

Depending on the detected operating state of the cryogenic storage device, different measures may be necessary for protecting the samples. Associated therewith, different residence times of the sample carrier device in the intermediate storage container can be expected. Short residence times of the sample carrier device in the intermediate storage container require temperatures that are not as low as the temperatures for long residence times. Therefore, for a short residence of for example five to ten minutes, the intermediate storage container is cooled only to −30° C. The intermediate storage container is accordingly cooled only to a predetermined temperature sufficient for the storage duration to be expected, before the sample carrier device is transported into the intermediate storage container cooled to the predetermined temperature. It is thus possible to avoid an unnecessarily high power consumption and coolant consumption.

An advantageous further development of the method according to the invention therefore comprises detecting a predetermined operating state of the cryogenic storage device, cooling the intermediate storage container by means of the intermediate storage cooling device to a predetermined temperature depending on the detected operating state, transporting the sample carrier device into the cooled intermediate storage container, and detecting the duration for which the sample carrier device is located in the intermediate storage container. If a maximum duration defined as a function of the predetermined temperature is exceeded, the intermediate storage container is cooled to a predetermined second temperature and/or an alarm signal is output. The duration for which the sample carrier device is located in the intermediate storage container is detected by a time measuring unit. As soon as a maximum storage duration for the temperature of the intermediate storage container is exceeded, an alarm signal may sound and/or the intermediate storage container may be cooled to a lower temperature which is sufficient for a longer storage duration. With this operating mode, it is possible for example to protect samples even when the elimination of a malfunction is unexpectedly delayed and thus the storage time of the samples in the intermediate storage container has to be extended.

If a further cooling of the intermediate storage container is not possible because cooling is already taking place at the maximum cooling power or a minimum temperature has already been reached, an acoustic or optical alarm signal may be output upon exceeding a maximum storage duration of e.g. twelve hours in the intermediate storage container.

BRIEF DESCRIPTION OF SEVERAL VIEWS OF THE DRAWINGS

The invention will be explained in more detail below with reference to the examples of embodiments shown in FIGS. 1 to 8. In the schematic figures.

DETAILED DESCRIPTION OF PREFERRED EMBODIMENTS

Figure 1:
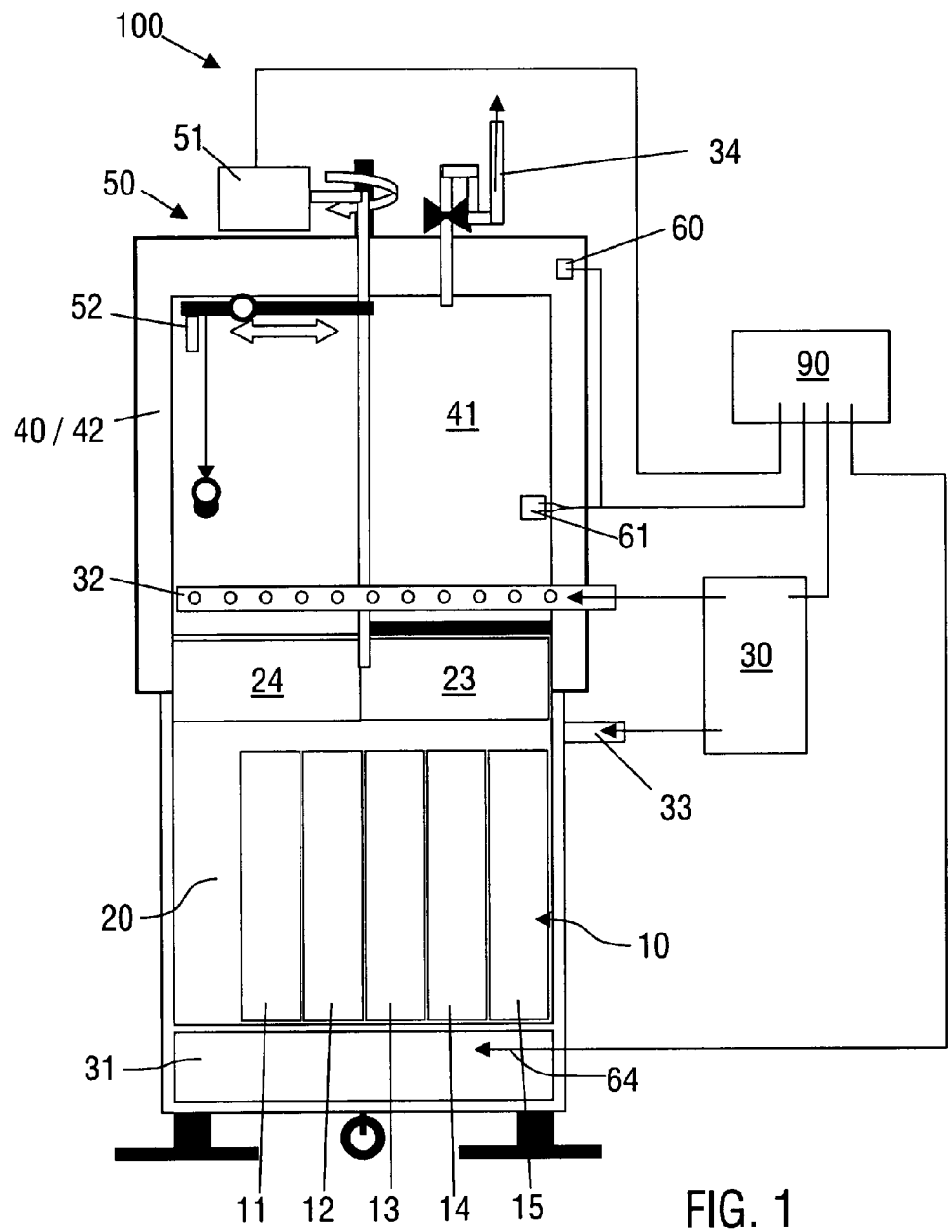
FIG. 1 shows a vertical sectional view of a cryogenic storage device according to the invention with a control unit.

The sectional view in FIG. 1 shows a cryogenic storage device 100 with a cryogenic container 20, comprising a cylindrical cryogenic tank with a wall thermally insulated by vacuum. A sample carrier device 10, comprising a plurality of carrier parts 11 to 15, is accommodated in the cryogenic container. A liquid bath 31 containing liquid nitrogen is arranged below the sample carrier device 10, so that the sample carrier device 10 in the gas phase is located above the liquid nitrogen bath. The liquid bath is supplied from a cooling device 30 by means of a refilling line 33 for liquid nitrogen. A filling lever sensor 64 serves for monitoring the quantity of nitrogen in the cryogenic container 20.

The cryogenic container 20 has at its upper end an opening which is closed by thermally insulated cover parts 23 and 24. An intermediate storage container 40 is arranged on the cryogenic container 20. The intermediate storage container 40 is adapted as a substantially cylindrical storage tower 42 with an opening on its underside. The storage tower 42 is seated on the cryogenic container 20 in such a way that the opening of the cryogenic container coincides with the opening of the storage tower 42 and is completely encircled by the wall of the storage tower 42 encircling the opening. Preferably, the storage tower 42 is seated so securely on the opening of the cryogenic container 20 that a substantially gas-tight connection is produced. A gas-tight closure of the intermediate storage container is particularly important when the latter is cooled to very low temperatures below −80° C., so as to avoid any formation of ice in the interior. The intermediate storage container 40 or the storage tower 42 is thermally insulated and is equipped with an intermediate storage cooling device 32. The latter comprises a cooling gas inlet, through which nitrogen gas can flow into the interior of the intermediate storage container. A gas outlet 34 is located at the upper end of the storage tower 42.

A transport device 50 comprising a winch 51 and a translation mechanism 52 is installed for transporting the sample carrier device 10 between the cryogenic container 20 and the storage tower 42. The cryogenic storage device 100 moreover has a sensor device 60 for detecting at least one operating parameter of the cryogenic storage device. By way of example, in FIG. 1, besides the filling level sensor 64 in the liquid nitrogen bath 31, a temperature sensor 61 is shown in the intermediate storage container 40. The sensors 61, 64 are connected to a control unit 90 which, based on the signals received from the sensors 61, 64, actuates the intermediate storage cooling device 32 and the transport device 50.

Figure 2:
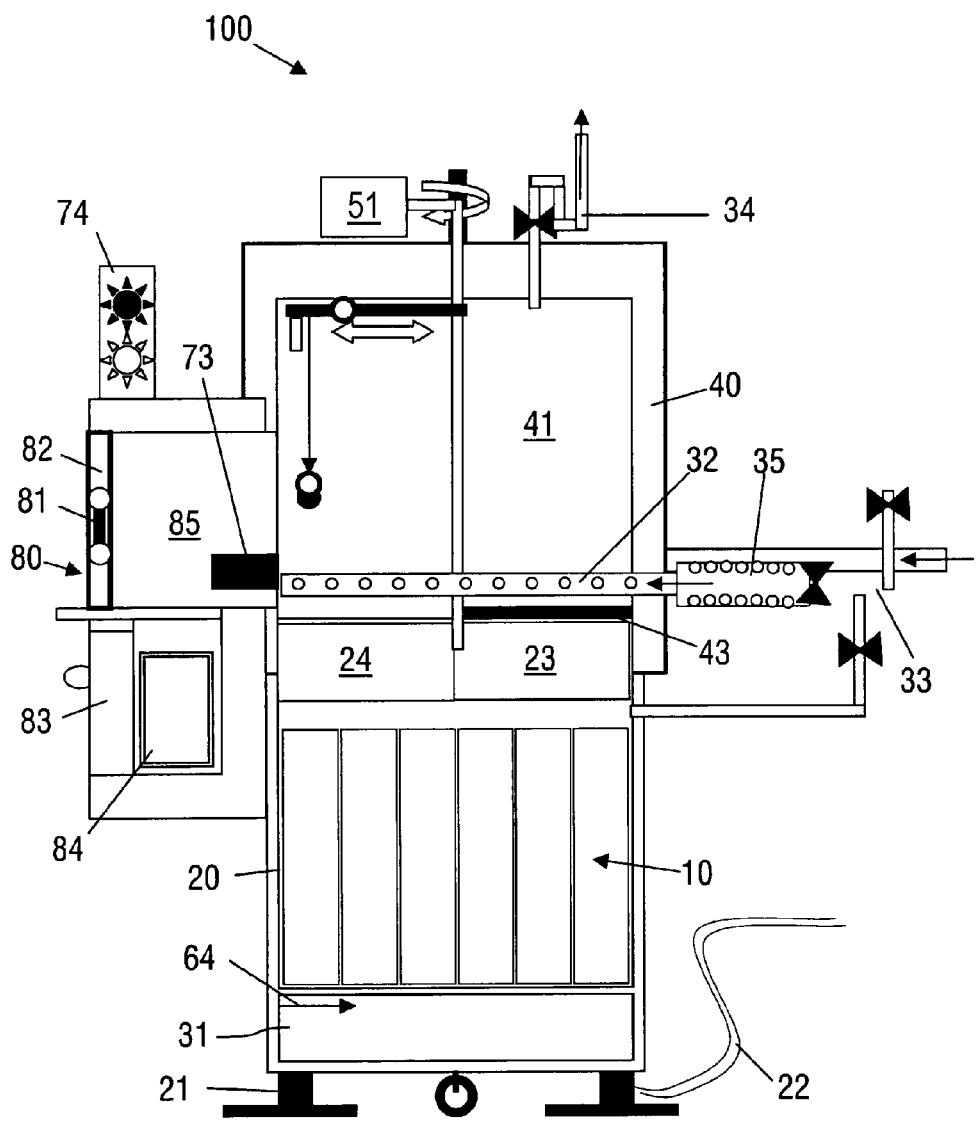
FIG. 2 shows a more detailed sectional view of a cryogenic storage unit according to the invention with a lock device.

The intermediate storage cooling device 32 is supplied by the same liquid nitrogen source as the cooling device 30 for the cryogenic tank 20, as shown in FIG. 2. The cooling of the intermediate storage container 40 takes place by the outflow of gaseous nitrogen. The intermediate storage cooling device 32 therefore has a heating device 35 for evaporating the liquid nitrogen.

The cryogenic storage device 100 shown in FIG. 2 moreover has a lock device 80 for introducing and removing cryogenic samples into and from the cryogenic storage device 100. The lock device 80 comprises a lock chamber 85 with a viewing window 82 and a hand access 81, as well as a door 83 for removing and introducing samples into and from the lock chamber. A receiving chamber for a transport container for cryogenic samples 84 is additionally provided. A barcode reader 73 serves for monitoring the transport of samples between the lock device 80 and the intermediate storage container 40. Fitted on the lock device 80 is an alarm indicator 74 which is able to indicate a malfunction state of the cryogenic storage device 100 by means of an optical and/or acoustic signal.

Figure 3:
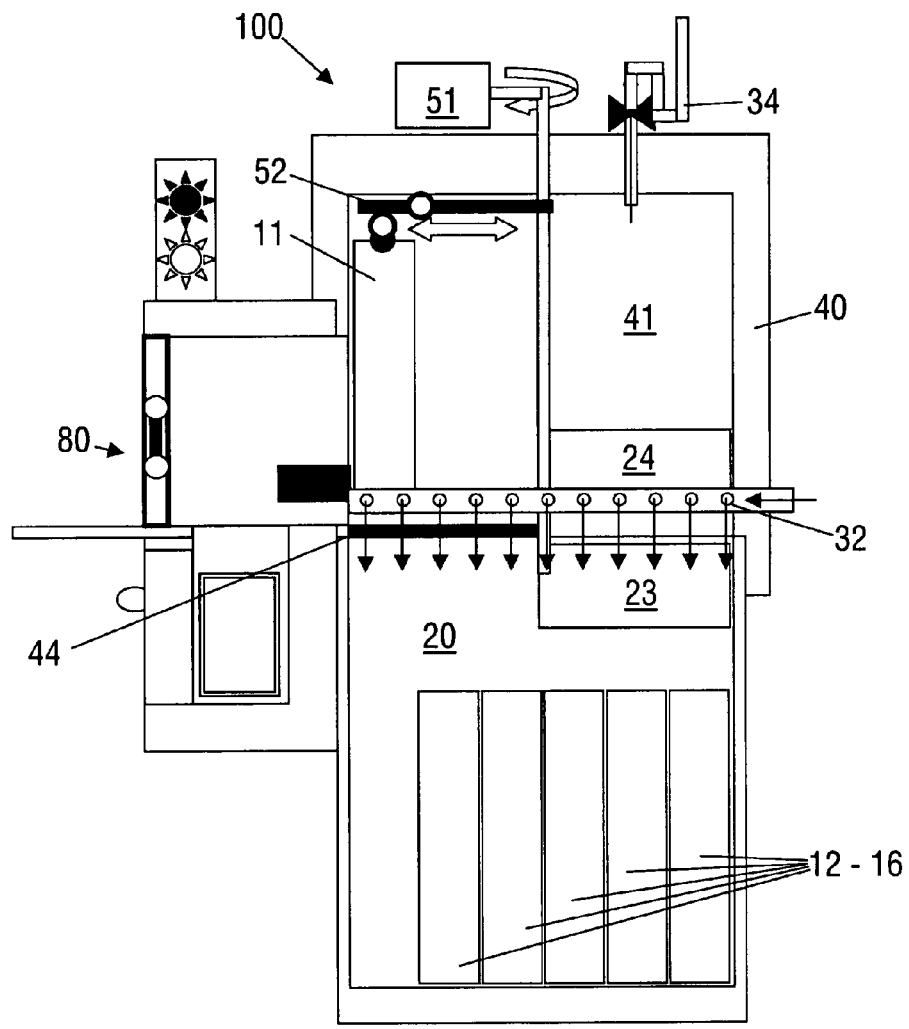
FIG. 3 shows a sectional view of a cryogenic storage unit according to the invention, in which one carrier part of the sample carrier unit is located in the intermediate storage container.

FIG. 3 shows a cryogenic storage device with an open cryogenic tank. One cover part 23 of the cryogenic tank is still in a closed position, while a second cover part 24 has been folded out from the closed position. In the case of the cryogenic storage device 100 shown in FIG. 3, the sample carrier device 10 comprises a plurality of carrier parts 11 to 16, of which one carrier part 11 is located in the intermediate storage container while the other carrier parts 12 to 16 are still located in the cryogenic tank. The carrier part 11 located in the intermediate storage container 40 is suspended by a coupling device on the translation mechanism 52 of the transport device. Below the carrier part in the intermediate storage container, a collecting plate 44 is arranged in the opening between the intermediate storage container 40 and the cryogenic tank 20 in order to collect any samples dropping down or, if necessary, to provide emergency insulation of the tank. The state of the cryogenic storage device 100 shown in FIG. 3 is assumed for example when an individual rack 11 is defective and must be replaced.

In order to replace the rack 11, the contents thereof are first transferred in a controlled manner. The intermediate storage container is then lifted away from the cryogenic container and displaced so that the defective rack 11 can be removed in the downward direction through the opening of the intermediate storage container 40 and can be replaced by a new rack. The cryogenic container 20 is advantageously closed beforehand in order to maintain the insulation. Once the defective rack has been replaced, the intermediate storage container 40 can be placed back onto the cryogenic container. In this case, the new rack is preferably cooled in the intermediate storage container before it is restocked with samples and transported into the cryogenic container, which has been reopened.

Figure 4:
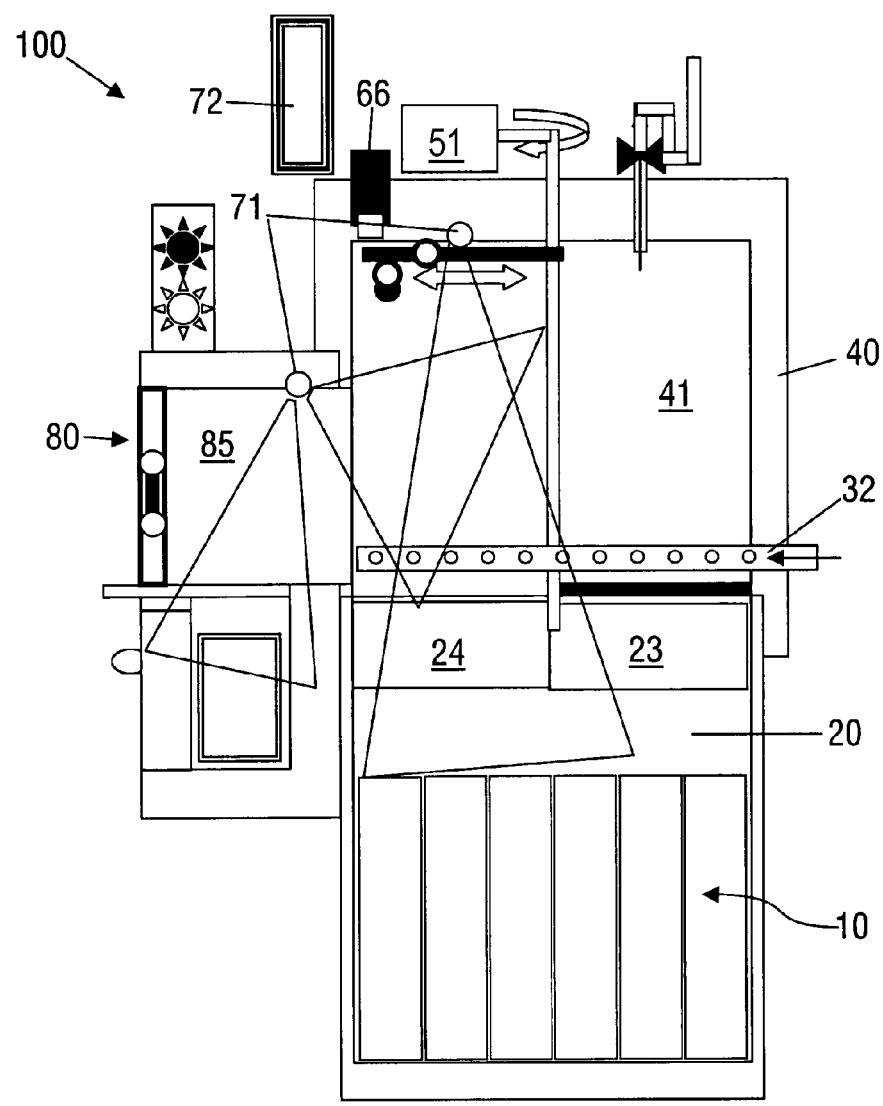
FIG. 4 shows a further sectional view of a cryogenic storage unit according to the invention, in which all the carrier parts of the sample carrier device are located in the cryogenic container.

FIG. 4 shows a sectional view of a cryogenic storage device 100 with a lock device 80 in the normal storage state, in which all the carrier parts 11 to 16 of the sample carrier device 10 are located in the cryogenic tank 20 which is tightly closed by the cover parts 23 and 24.

In order to be able to monitor samples during storage in the intermediate storage container 40 or in the lock 80, lamps 71 are located in the lock chamber 85 and in the intermediate storage container 40 in order to illuminate the lock chamber 85 and the interior of the intermediate storage container. The illuminated zones are shown by way of example in FIG. 4. In addition, a camera device 66 is provided for recording images of the interior of the intermediate storage container. The image data recorded by the camera can be displayed on a monitor 72.

Figure 5:
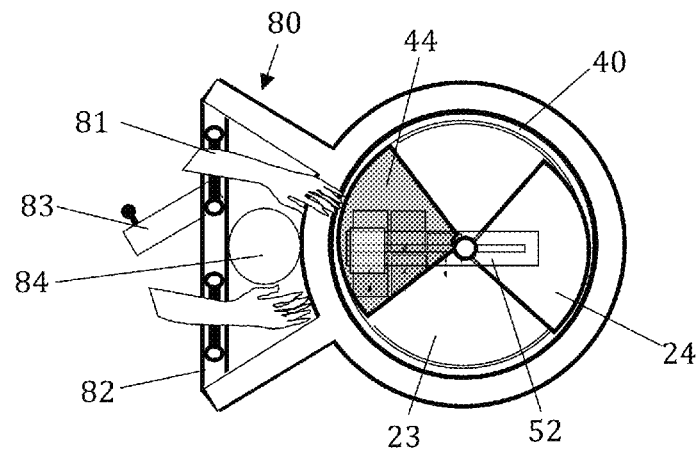
FIG. 5 shows a horizontal sectional view through a cryogenic storage device according to the invention with a lock device and two hand accesses.

Given a substantially cylindrical cryogenic tank 20 and intermediate storage container 40, the closure parts 23, 24 of the cryogenic tank and the intermediate storage closure device 43 of the intermediate storage container 40 may be sector-shaped, as shown for example in the sectional view in FIG. 5. The cover parts 23, 24 and 44 are rotatable about a vertical central axis of the cylindrical cryogenic container and intermediate storage container. It is possible to see in FIG. 5 a collecting plate 44 as part of an intermediate storage closure device 43 and a closure part 24 of the cryogenic tank 20. In the drawing, it is possible to see in a schematic manner therebelow the samples arranged in the cryogenic tank and a rail of the translation mechanism 52 in the intermediate storage container 40.

The embodiment of the cryogenic storage device shown in FIG. 5 has a lock device 80 which is arranged with a sector shape on the outside of the intermediate storage container 40 and is closed off by a flat viewing window 82. The lock device 80 has a door 83 and a sample holder 84 for holding a transport container for cryogenic samples. The lock device 80 has two hand accesses 81, through which a user can reach into the lock chamber 85. The hand accesses may be equipped with safety gloves which protect the hands of the user against cold, and the lock chamber 85 against contamination.

Figure 6:
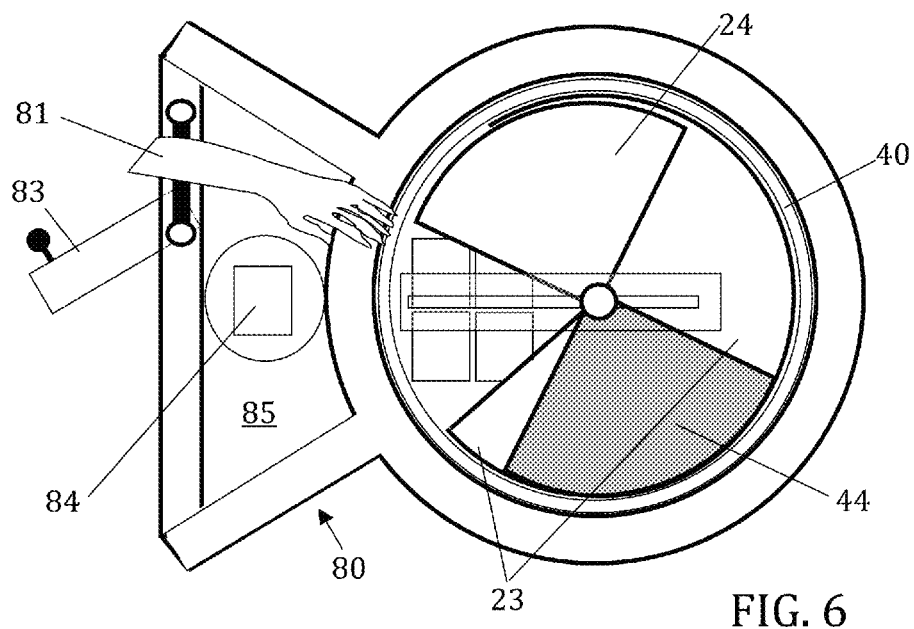
FIG. 6 shows a horizontal section through a cryogenic storage device according to the invention with a lock device and a hand access.

FIG. 6 shows a variant of the cryogenic storage device with just one hand access 81 for the lock chamber 85. The sector-shaped cover parts can also be seen in FIG. 6, wherein one cover part 24 covers one quarter of a circle and one cover part 23 covers three-quarters of a circle.

Figure 7:
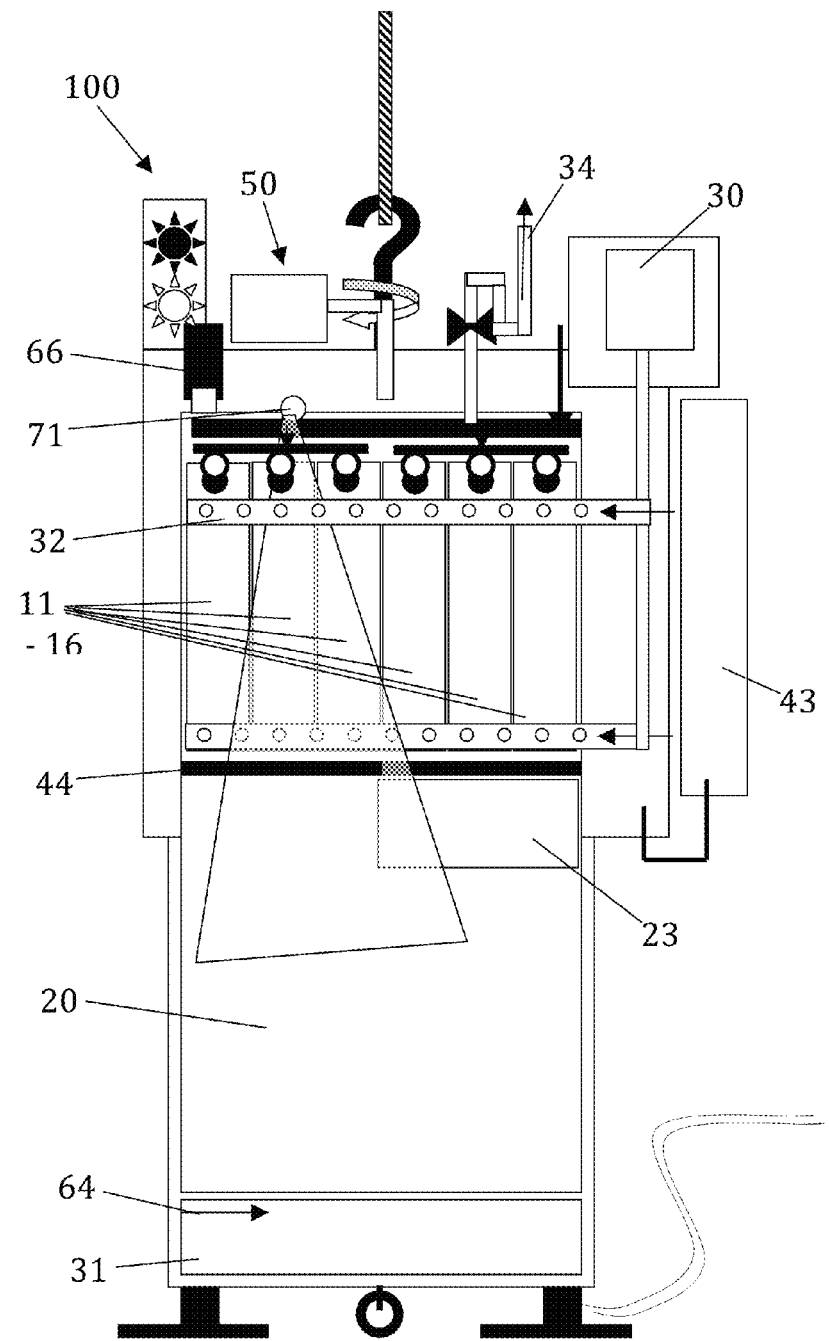
FIG. 7 shows a vertical section through a cryogenic storage device according to the invention in the malfunction state, in which the entire sample carrier device is located in the intermediate storage container.

FIG. 7 shows a cryogenic storage device 100 according to the invention, in which all the carrier parts 11 to 16 of the sample carrier device 10 are located in the intermediate storage container 40. All the carrier parts 11 to 16 are suspended on a coupling device of the transport device 50. The cryogenic tank 20 is half-open. An intermediate base 44 closes the intermediate storage container at the bottom. The intermediate storage cooling device 32 is being supplied with nitrogen by the cooling device 30. An intermediate storage closure device 43, which is provided for closing the intermediate storage container in a full and insulated manner, is folded open on the outside of the intermediate storage container. In the case of the cryogenic storage device 100 according to the invention and in the method according to the invention, the state shown in FIG. 7 is assumed for example in the event of a malfunction when, due to overfilling of the liquid nitrogen bath 31 at the bottom of the cryogenic tank 20, there is a risk to the cryogenic samples stored in the sample carrier 10. This state can also be assumed as a precautionary measure when refilling the cryogenic container 20 with liquid nitrogen.

An overfilling with liquid nitrogen is detected as an operating state for example on the basis of a signal from the filling level sensor 64 in the liquid bath 31 and on the basis of an operating state of the cooling device 30 by means of a throughflow sensor. If the "overfill" operating state is ascertained on the basis of the detected operating parameters, the intermediate storage cooling device 32 is activated and the cooling of the intermediate storage container 40 is started and the sample carrier device 10 is transported into the intermediate storage container 40. An alarm signal may additionally be output at the same time.

Figure 8:
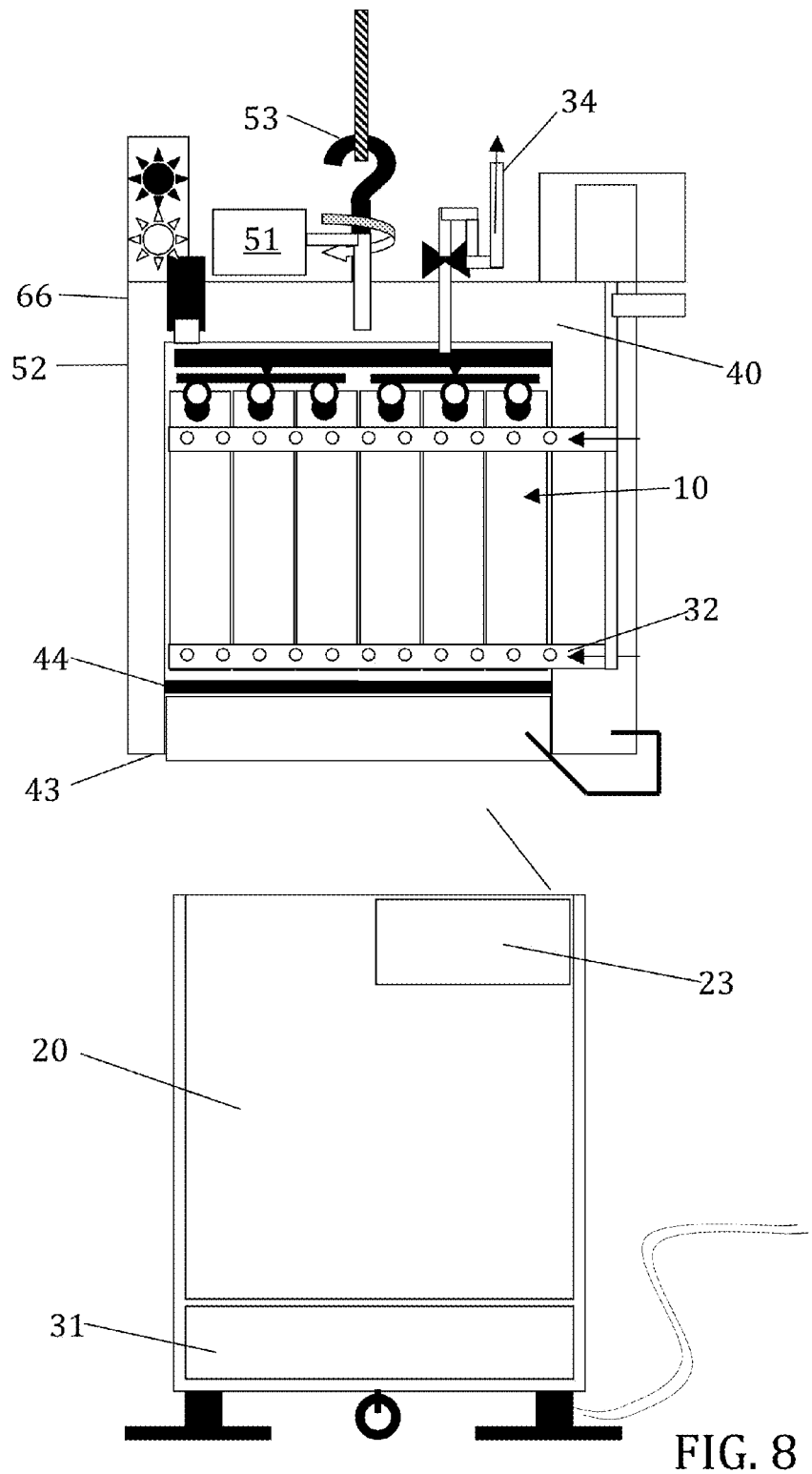
FIG. 8 shows a vertical sectional view through a cryogenic storage device according to the invention in the malfunction state, in which the sample carrier device is located in the closed intermediate storage container, and in which the intermediate storage container and the cryogenic container are spatially separated from one another.

FIG. 8 finally shows the cryogenic storage device 100 of FIG. 7, in which the intermediate storage container 40 is lifted away from the cryogenic container 20 by means of a lifting device 53 with the intermediate storage closure device 43 in the closed state. The intermediate storage container is now cooled and insulated independently and is suitable for the short-term storage of cryogenic samples depending on the temperature it its interior 41. During this time, the cryogenic tank 20 may for example be replaced or repaired or an overfilling with liquid nitrogen can be eliminated. In the interim period, the cryogenic samples are safely stored in the cooled intermediate storage container 40. A rapid and uncontrolled removal of the cryogenic samples into an atmosphere at room temperature is not necessary. Undesirable effects on the samples, such as mechanical vibrations or heating of the samples and ice formation, are avoided as a result.

The invention claimed is:

1. A cryogenic storage device suitable for cryogenic storage of biological samples, said cryogenic storage device comprising:
   (a) a sample carrier device which is adapted to accommodate the samples,
   (b) a cryogenic container which is adapted to accommodate the sample carrier device,
   (c) a container cooling device adapted to cool the cryogenic container,
   (d) an intermediate storage container adapted for intermediate storage of the sample carrier device,
   (e) a transport device adapted to move the sample carrier device between the cryogenic container and the intermediate storage container,
   (f) a sensor device adapted to detect at least one operation parameter of the cryogenic storage device,
   (g) a control device in communication with the sensor device and the transport device forming a control loop therefrom, the control device being configured to detect a predetermined malfunction operation state of the cryogenic storage device and to automatically send control signals for activation purposes to the transport device based on the detected predetermined malfunction operation state, and
   (h) an intermediate storage cooling device configured to cool the intermediate storage container, wherein the intermediate storage cooling device is activated as a function of an output signal from the sensor device upon detection of the predetermined malfunction operation state, and the transport device is activated as a function of the output signal from the sensor device upon detection of the predetermined malfunction operation state of the cryogenic storage device, so that the sample carrier device is moved from the cryogenic container into the cooled intermediate storage container, and
   the predetermined malfunction operation state includes at least one of an overfilling of the cryogenic container with liquid nitrogen, and undue heating of the samples in the cryogenic container, diminishing insulation of the cryogenic container, a rack defect, and a cryogenic container defect.

2. The cryogenic storage device according to claim 1, in which the sensor device comprises at least one of sensor type selected from the group consisting of:
   a sample carrier temperature sensor which is adapted to detect a temperature on the sample carrier device,
   a container temperature sensor which is adapted to detect a temperature in the cryogenic container,
   an intermediate storage temperature sensor which is adapted to detect a temperature in the intermediate storage container,
   a coolant sensor which is adapted to detect a coolant consumption of the cooling device, a filling level sensor in the cryogenic container,
   a throughflow sensor which is adapted to detect an operation state of a coolant valve of the cooling device,
   a camera device which is adapted to record images in the intermediate storage container and/or in the cryogenic container,
   a pressure sensor which is adapted to detect a negative pressure in an evacuated wall of the cryogenic container,
   a sample carrier test sensor which is adapted to detect an operation state of the sample carrier device,
   a gas sensor for detecting a gas composition in at least one of the cryogenic container and the intermediate storage container, and
   a time measuring unit for detecting a duration during which the sample carrier device is located in the intermediate storage container.

3. The cryogenic storage device according to claim 1, further comprising a lock device which is adapted for at least one of introducing and removing samples into and from the intermediate storage container.

4. The cryogenic storage device according to claim 1, in which the intermediate storage container comprises:
   a storage tower which is arranged on an upper side of the cryogenic container, and
   an intermediate storage closure device adapted to close an interior of the storage tower.

5. The cryogenic storage device according to claim 4, in which the transport device comprises at least one of
   a winch which is arranged at an upper end of the storage tower,
   a robot arm, and
   an extendable rod.

* * * * *